United States Patent [19]

Markus et al.

[11] Patent Number: 5,405,755
[45] Date of Patent: Apr. 11, 1995

[54] METHOD AND APPARATUS FOR DETECTING SEPSIS CAUSATION IN A CATHETER

[75] Inventors: Stanley Markus; Robert Brewer, both of Oconomowoc, Wis.

[73] Assignee: Daymark Medical Industries, Inc., Pewaukee, Wis.

[21] Appl. No.: 128,901

[22] Filed: Sep. 29, 1993

Related U.S. Application Data

[63] Continuation-in-part of Ser. No. 51,420, Apr. 23, 1993.

[51] Int. Cl.$^6$ .......................... C12Q 1/04; C12M 1/28; A61B 10/00
[52] U.S. Cl. ...................... 435/34; 128/756; 472/294; 435/31; 435/294
[58] Field of Search .......... 15/104.05, 104.2; 128/749, 756, 759; 422/294; 435/31, 34, 294, 295

[56] References Cited

U.S. PATENT DOCUMENTS

| | | | |
|---|---|---|---|
| 2,701,559 | 2/1955 | Cooper | 128/756 |
| 4,235,244 | 11/1980 | Abele | 128/749 |
| 4,368,272 | 1/1983 | Kashket | 435/293 |
| 4,397,945 | 8/1983 | Lemonnier | 435/31 |
| 4,485,824 | 12/1984 | Moll | 128/756 |
| 5,091,316 | 2/1992 | Monthony | 435/295 |
| 5,240,675 | 8/1993 | Wilk | 422/22 |
| 5,260,020 | 11/1993 | Wilk | 422/22 |

OTHER PUBLICATIONS

Markus S., Culturing Indwelling Central Venous Catheters In Situ, Infections in Surgery, May 1989, pp. 157–162.
Beam, T., Vascular Access Catheters & Infections, Infections in Surgery, vol. 8 No. 5 May 1989, pp. 156, 161.
Markus, Stan, Buday, Stephen, "Culturing Indwelling Central Venous Catheters In Situ", *Infections in Surgery*, May, 1989, pp. 157–162.

*Primary Examiner*—Michael G. Wityshyn
*Assistant Examiner*—Ralph Gitomer
*Attorney, Agent, or Firm*—Blakely, Sokoloff, Taylor, Zafman

[57] ABSTRACT

A method and an apparatus is disclosed for detecting whether a catheter is the cause of an infection in a patient without removing the catheter from the patient. The apparatus includes a wire handle, brush and a protective, microbially impervious bag disposed over the handle and brush. In use, the apparatus is connected to a catheter, the brush is advanced through the catheter, and simultaneously removed from the protective bag. The apparatus is then withdrawn from the catheter, and simultaneously back into the bag, and the bag is capped to maintain the proper humidification of an fibrin sample obtained so that the microbes thus obtained remain viable.

10 Claims, 7 Drawing Sheets

METHOD AND APPARATUS FOR DETECTING SEPSIS CAUSATION IN A CATHETER

RELATED CASES

This is a continuation in part of U.S. patent application Ser. No. 08/051,420, filed on Apr. 23, 1993.

BACKGROUND OF THE INVENTION

1. Field of the Invention

The present invention relates to a method and an apparatus for detecting whether a catheter is the cause of sepsis in a patient without unnecessarily removing the catheter from a patient.

2. Art Background

For a number of years, central venous catheters have been used widely in medicine in the critical care area. These catheters are commonly used to perform a number of different, but equally important functions, among which include (a) measuring central pressure;
(b) monitoring and modifying fluid volume;
(c) administering one or more therapeutic substances simultaneously;
(d) providing a secure site of intravenous ("IV") access; and
(e) conducting blood therapy.

Furthermore, these catheters also are used in long-term treatment, such as chemotherapy and parenteral nutrition (so called "Hickman catheter").

Venous catheters are inserted into a patient "peripherally" through a cephalic or basilic vein, or "centrally" through the internal jugular, external jugular, subclavian or saphenous vein. Determining which type of insertion is based on many factors; however, any type insertions typically causes at least some discomfort and pain to the patient, and requires a reasonable amount of skill, and each insertion is subject to certain inherent risks and costs. In addition to venous catheters, there are also peritoneal catheters, urethral catheters, such as the Foley catheter, and arterial catheters in the prior art.

According to various studies, approximately 4–15% of the venous catheters are the cause of secondary infections. On the average, in about 60% of the cases in which there is sepsis, the catheter cannot be ruled out as the cause, and the catheter is removed to make a determination if it is the cause, as described in more detail below. Even though only a small percentage of catheters are the cause of such infections, hospitals are required to continuously monitor catheters for possible catheter sepsis (i.e., infections within an indwelling line of a catheter) which may cause complications in a patient's treatment leading to sickness or even death.

The current diagnostic techniques used to detect catheter sepsis are problematic. If a physician or nurse suspects that an infection is being caused by the catheter, the suspect catheter is removed and replaced with a new catheter. The tip of the suspect catheter is removed under sterile conditions and sent to the lab for contamination testing. If the catheter is found to be infected, physicians can provide treatment in accordance with standard medical procedures for such infection.

This procedure, called a "tip culture", offers a number of disadvantages. The primary disadvantage is that since only a small percentage of the catheters become infectious, patients quite often experience additional pain and discomfort due to the unnecessary removal of the catheters. Also, the insertion of a new catheter can be associated with additional risks of infection, such as bleeding, pneumothorax, and infection. Moreover, the removal of non-infected catheters contributes to rising medical costs.

One prior art method of identifying and locating dental microorganisms is disclosed in U.S. Pat. No. 4,368,272 comprising a flexible strip of material with a sterile velvet material that is contacted with the teeth and then cultured.

Another prior art test method and apparatus for testing whether there is any infectious material in the contents in syringe is described in U.S. Pat. No. 4,397,945, which teaches the use of a sampling device for sampling a portion of the contents of the syringe.

Also in the prior art are cytology brushes which are used to collect cells for analysis. It is not believed that such a brush has heretofore been used for a sampling system for microbial infection.

Another prior art method previously developed by the present inventor is described in a publication entitled Markus, Stan and Buday, Stephen, "Culturing Indwelling Central Venous Catheters In Situ," Infections in Surgery, May 1989, pp. 157–160, and a review article Beam, Thomas, "Vascular Access, Catheters and Infections," *Infections in Surgery*, May 1989, pp. 156; 161–162. The Markus, et al. article teaches a method and apparatus for assessing whether central venous catheters is causing catheter sepsis in situ. The apparatus comprises a thin wire with either a stop or separate handle on or near one end, and a brush at the other end. The apparatus is specifically designed so that it cannot protrude through the end of the catheter. The brush is designed to fit the exact length of the catheter in situ, and a metal stopper ensures that the brush does not go beyond the catheter tip and does not damage the vein wall during sampling. (See FIG. 2 at p. 158).

Thus, there is a need for a better method and apparatus for determining the existence of infections being caused by an indwelling catheter, which method and apparatus do not have the drawbacks of the prior art.

SUMMARY OF THE INVENTION

A method and apparatus are disclosed which overcome the disadvantages and limitations associated with prior art tip culture testing techniques used to detect the presence of infections within the indwelling line of the catheter.

It is the object of the present invention to provide a method and an apparatus for detecting whether an infectious microbiological culture is present within an indwelling line of a catheter without removing the catheter from the patient.

It is also an object of the present invention to provide a method and an apparatus which would greatly reduce morbidity caused by an infection within a catheter by allowing physicians and nurses to easily monitor the suspect catheter.

It is a further object of the present invention to provide a cost-efficient method and apparatus for detecting an infection within a catheter without unnecessary removal and subsequent disposal of the catheter.

It is also an object of the present invention to avoid unnecessary pain and discomfort to a patient caused by removing a suspect catheter and replacing it with a new catheter.

These and other objects of the present invention are provided in a method and an apparatus for detecting an infection within a catheter without removing the catheter from the patient. The present invention provides a method for detecting an infection in a catheter comprising the steps of (i) supplying a specimen collection means adapted to fit within the interior of a catheter and collect any infectious microorganisms from the inside as well as the exterior of the end of the catheter; (ii) inserting said specimen collection means into said catheter to collect said microorganisms disposed with the catheter and the outside of the tip of the catheter; (iii) advancing said specimen collection means through said catheter towards the end of said catheter within the vein to a point where a portion of the specimen collection means passes through the end of the catheter and contacts the outer end of the catheter in order to sample the outside of the catheter as well as the inside; (iv) removing said specimen collection means from said catheter under sterile conditions so that a microbial specimen may be obtained on said specimen collection means; and (v) culturing said specimen to determine whether infectious microorganisms are present and identify the same.

In another embodiment of the present invention, the specimen collection means is disposed in a sterile container comprising an impervious flexible bag having a luer-lock connector on the end thereof and a cap disposed over the connector, which may also have a luer-lock connection. Upon removal of the cap, the luer-lock connector at the end of the flexible bag can be connected to the standard luer lock connector of a catheter. The specimen collection means is then advanced through the catheter as described above. However, the specimen collection means remains inside the bag until it is fully inserted into the catheter. It is then withdrawn from the catheter, and is never exposed to outside air, and consequently, never risks contamination from anything other than the catheter which is being sampled. Upon complete removal of the specimen collection means, the end is retained in the bag which serves to prevent extraneous contamination. Also, by closing the cap over the end of the bag, the volume inside the bag is sealed, preventing any moisture loss. As a result, the specimen taken from the catheter remains moisturized, and consequently, does not dry out. This preserves the viability of the sample if a microorganism is present.

The specimen collection means collects fibrin which may be coating inside and outside the tip of the catheter, the fibrin having mixed therein microbes which may then be cultured and identified. The fibrin along with the captured microbial sample can be plated under sterile conditions which are commonly known in the art and the cultures which may grow from the sample can be identified by known microbiological techniques.

Further, in one embodiment, the apparatus comprises a loop handle, and means for collecting said specimen within a catheter. The means for collecting said specimen is preferably a brush made of thin synthetic bristles. The length of the bristles is greater for the bristles at the end of the brush so that they protrude out the end of the catheter to take a sample outside the end of the catheter. The tip of the brush is blunted, rounded or otherwise dulled so that if it contacts the wall of the vein it does not damage the vein wall (or the wall of any other tissue which it may contact if used with other types of catheters.) The handle consists of a twisted wire loop in a manner so that the apparatus is advanced through the catheter a limited amount and prevented from passing through the catheter and beyond the proximal end. This prevents any chance of fragmentation with loss of brush within the catheter or vein.

In the presently preferred embodiment of the present invention, the apparatus further comprises a cover, and most preferably, the cover is in the form of a slim profile, sterile bag which fits over the entire apparatus, and is sealed at the insertion end by a luer lock assembly with a luer lock cap disposed over the end. The other end of the slim profile bag may be, but is not necessarily, attached to the handle end of the apparatus. The bag provides numerous advantages, and makes the use of the device easier and safer. The bag maintains the device in a sterile condition until it is ready for use. When the user is ready to use the apparatus, the luer-lock cap is removed, and the luer-lock coupling is coupled with the luer-lock of the catheter assembly with any substantial risk that the sample collection device will be contaminated. Once coupled to the catheter, the sample collection apparatus is advanced through the catheter until the apparatus is inserted as required to obtain the sample. Thereafter, the apparatus is withdrawn from the catheter and back into the bag. When the apparatus is fully withdrawn, the cap is placed back on the bag. This keeps the apparatus from becoming contaminated, and also keeps the apparatus, and any culture obtained thereby, in a humid condition, is maintained in the humid condition so that any microbial culture thereon remains viable.

The present apparatus can be used with a number of different types of catheters including indwelling venous catheters, Foley catheters, Hickman catheters, parenteral catheters, arterial catheters and the like.

BRIEF DESCRIPTION OF THE DRAWINGS

The objects of the present invention will be described with respect to the following figures in which.

DETAILED DESCRIPTION OF THE INVENTION

A method and an apparatus are described which are useful in detecting whether a catheter is causing an infection in a patient. The preferred embodiment of the present invention might best be described as an unique method for detecting an infection within a catheter through use of an apparatus (hereinafter referred to as a "culturing brush"), so that removal of the suspect catheter from a patient is not necessary unless it is determined that the catheter is the cause of the patient's infection. Such method and apparatus eliminates many disadvantages associated with using the conventional tip culture method for testing for infections within an indwelling line of a catheter. It should be borne in mind that the present invention need not be limited in use for central venous catheters, but may find wide application for testing any fluid conveying channel.

Figure 1:
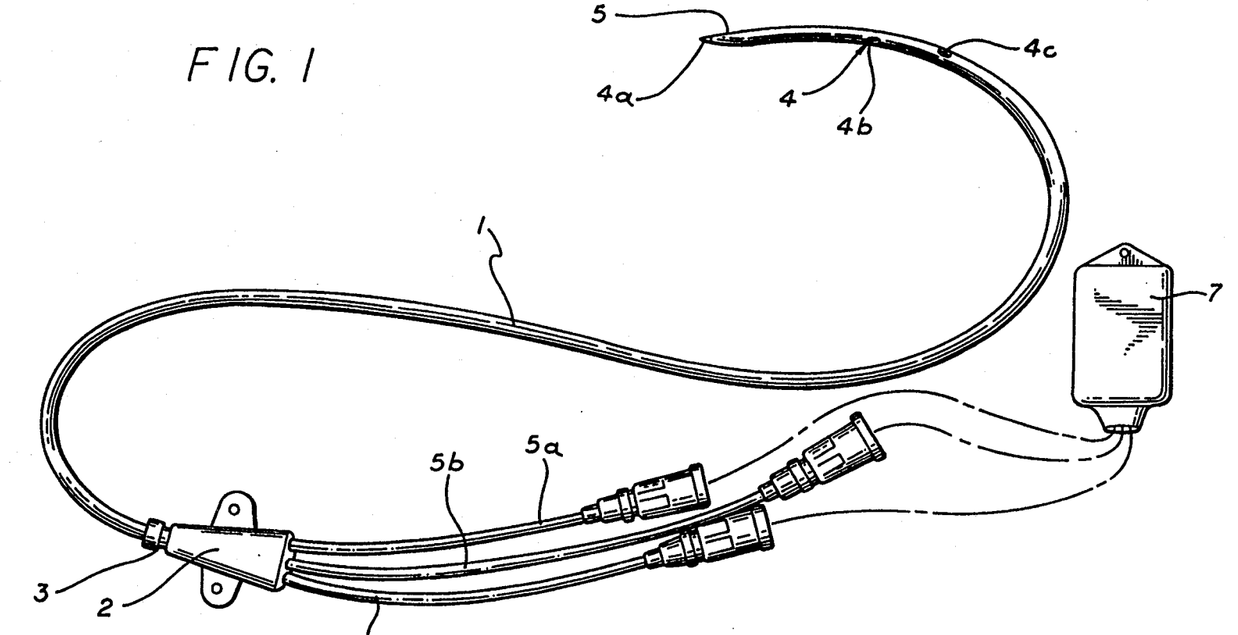
FIG. 1 is an illustration of a central venous catheter in the prior art.

FIG. 1 shows an embodiment of a prior art central venous catheter. The catheter comprises a central line 1 connected to a flexible hub 2. The central line is a tubular structure with an inlet 3 at the proximal end, connected to the flexible hub 2 and at least one outlet 4 located at the distal end 5 of the central line 1. In FIG. 1, there are three outlets labeled 4a, 4b and 4c in which therapeutic fluids are passed through and injected into a patient's vein. A plurality of lumen extension tubes, shown as 5a, 5b and 5c, provide a connection between an intravenous supply 7 and the flexible hub 2 to allow therapeutic fluids to be given to a patient intravenously.

Figure 2:
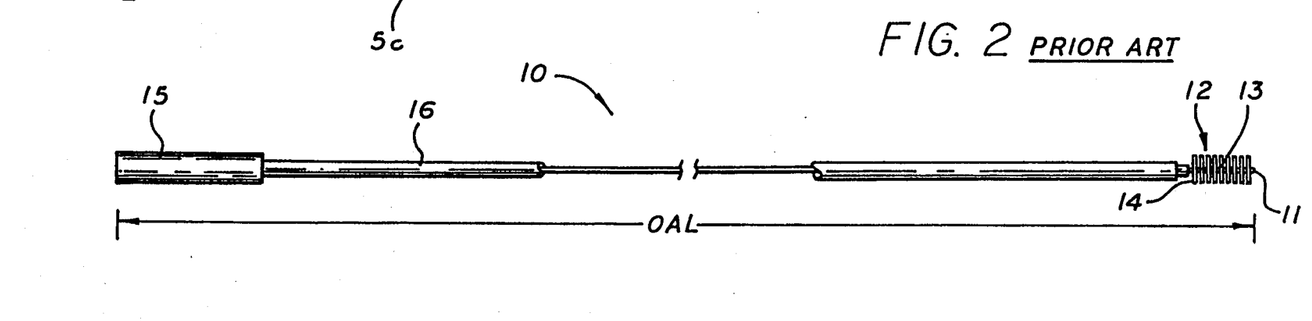
FIG. 2 is a sectioned view of a prior art embodiment of the fibrin sampling device of the prior art.

Referring now to FIG. 2, a prior art embodiment of a culturing brush described in the above-referenced Marcus, et al. article is illustrated. The culturing brush 10 has an overall length of 18 centimeters ("cms") with a tolerance of 0.50 cm. The brush tip 12 included a stem 13 and a plurality of bristles 14 and end 11. The stem 13 was a stainless steel wire having a diameter of 0.010 in. The plurality of bristles 14 protrude radially out from the stem 13 to collect the fibrin deposited on an inner surface of an indwelling line of a catheter. Each of the plurality of bristles is made of nylon material, such as Tynex®, or other suitable bristle material, and has a diameter of about 0.005 in.. The overall brush has a diameter of 5 mm±0.5 mm and a length of 13 mm±1 mm. The brush stem 13 extends through a spring sheath 16 and is bonded into a handle 15.

Figure 5:
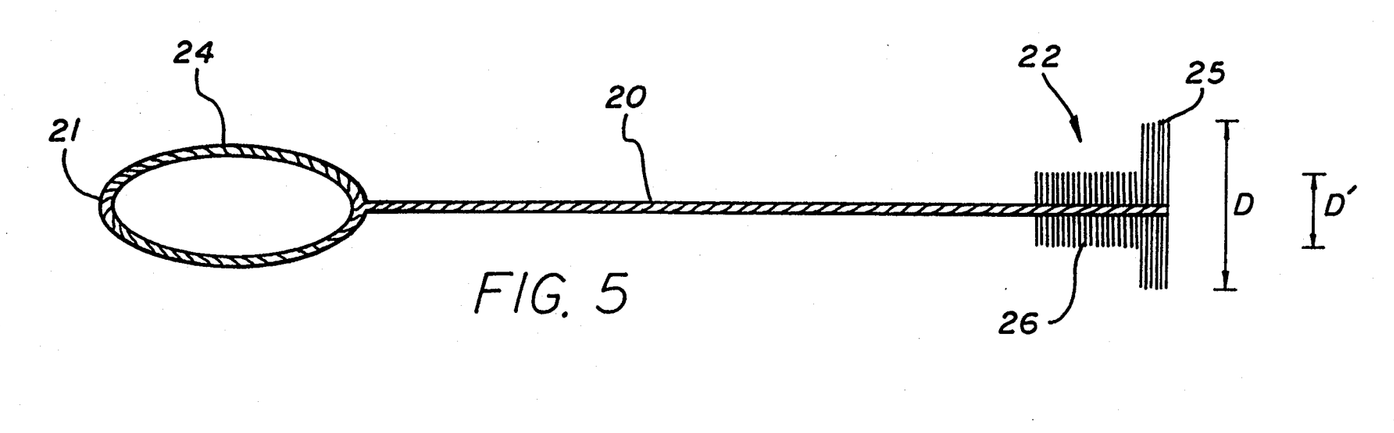
FIG. 5 is a side view of an alternative embodiment of a microbiological fibrin sampling brush of the present invention.

FIG. 5 is the presently preferred embodiment of the present invention comprising a flexible stainless steel twisted wire 20 having a brush 22 on one end and a loop handle 24 made of the untwisted portion of the stainless steel on the other end. The end 21 is blunted or rounded for safety. In this embodiment, the preferred dimensions include the diameter of the wire being 0.038 inches±0.003 inches, the overall length being 12, 14 or 18 inches, depending upon the size of the catheter in which it is used, and the bristles may be 0.003 Tynex, but are preferably 0.0025 inch width nylon. The longer bristles 25 display a 3 mm diameter D, and extend along the length of the brush for about 2 mm. The shorter bristles 26 have a diameter D' of 1.5 mm and extend along the length of the brush for about 6 mm for a total length of brush of about 8 mm. Another way of describing the length of the bristles is that the longer bristles are of sufficient length that their effective diameter (the apparent diameter when viewing the longer bristles from the end) is greater than the diameter of the catheter, or another way, is that the length of any such bristle is longer than the radius of the catheter. The shorter bristles have an effective diameter approximating the inner diameter of the catheter, or another way to describe it, is that the length of the shorter bristles is approximately the inner radius of the catheter.

Figure 6:
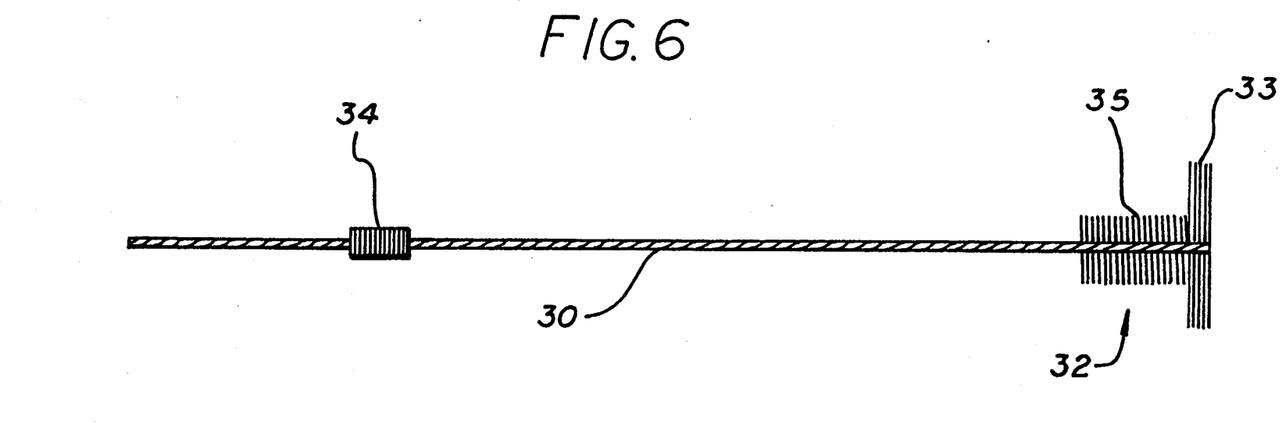
FIG. 6 is a side view of an alternative embodiment of a microbiological fibrin sampling brush of the present invention.

FIG. 6 is yet another embodiment of the present invention comprising a flexible stainless steel twisted wire 30 having a brush 32 on one end 31, which is rounded, and a stop means 34 made of stainless steel, to stop the brush from passing too far through the catheter. Again, the brush 32 is made up a longer bristle section 33 and a shorter bristle section 35.

Additional lengths of the device may be required for different lengths of catheters. For a standard indwelling venous catheter, lengths of 15, 20 and 30 cms are required. For a standard Hickman catheter, a length of 36 inches is required. It will be obvious to a person of ordinary skill in the art to modify the length, and adapt the brush diameter to accommodate various catheter sizes as required.

Figure 3:
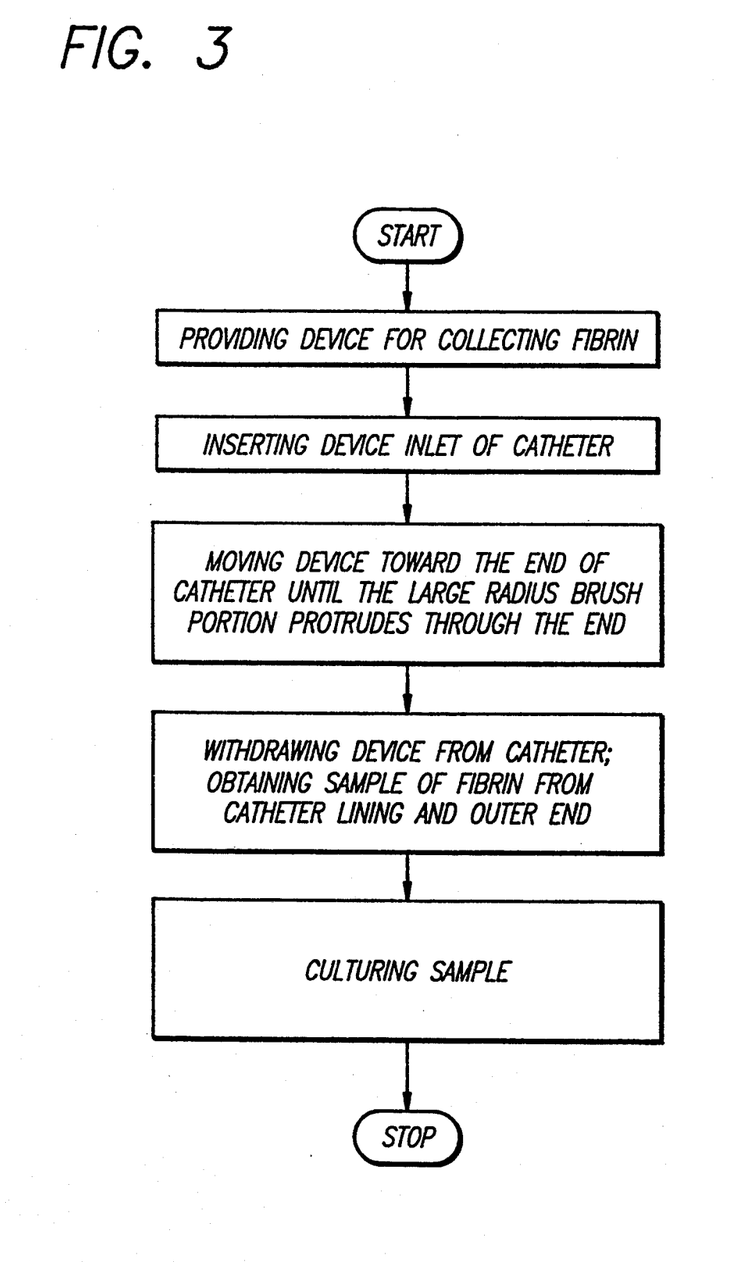
FIG. 3 is a flowchart illustrating a method for determining the existence of an infection by sampling inside the catheter and outside the tip of a catheter.

FIG. 3 illustrates procedure for determining whether an infection exists in the indwelling of the central line of the central venous catheter. The first step is to obtain the culturing brush as illustrated in FIGS. 5 or 6 (Step 1). A brush of the proper size must be selected so that the brush can be advanced to, and just through the tip of the catheter. The patient is then prepared and draped, and the physician gloved with sterile gloves. The IV is then disconnected. Next the distal end of the catheter is sterilized. Next, the culturing brush is inserted into the flexible hub of the catheter (Step 2). By applying force to the culturing brush, the brush tip passes through an inlet of the indwelling central line towards the tip of the catheter (Step 3). As a result, the plurality of bristles of the brush tip come into contact with the inner surface of the indwelling line of the catheter. As the brush tip approaches the tip of the catheter, the handle permits the brush tip to just protrude through the tip of the catheter because the diameter of the handle is larger than the diameter of the catheter end. In the embodiments shown in FIGS. 5 and 6, the loop handle 24 and the stop means 34 serve the same purpose at the end of the catheter. Thereafter, the brush is removed from the indwelling line of the catheter (Step 4) bringing with it a sample of fibrin collected on the interior wall of the catheter and the outer tip of the catheter, said fibrin having captured within it a sampling of any microbiological contamination which may exist in the catheter. The brush tip is then cultured by applying the brush to a culture media under sterile conditions (Step 5). Alternatively, the brush is secured in a sterile container and sent to a laboratory for culturing. The IV is then reconnected and restarted.

Figure 4:
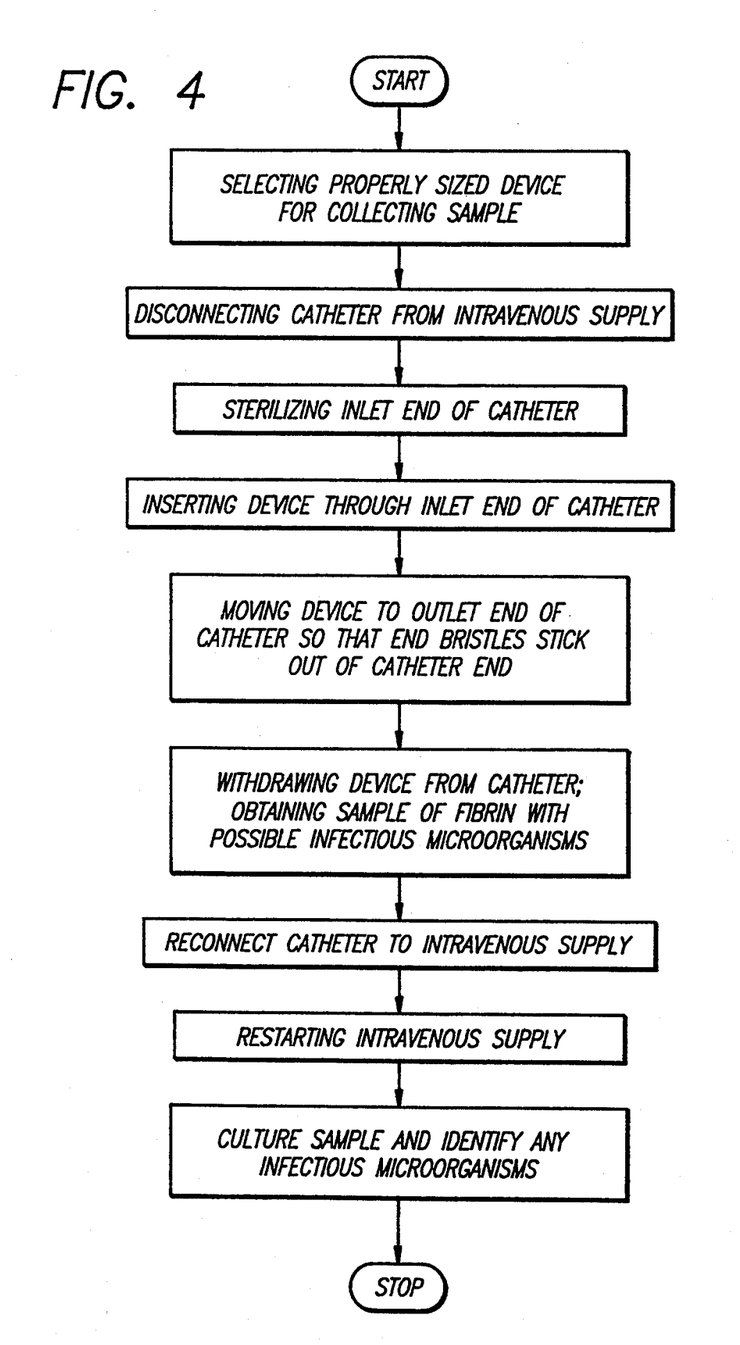
FIG. 4 is a more detailed flowchart of the method for testing the existence of an infection by sampling inside the catheter and outside the tip of a catheter.

Referring to FIG. 4, another embodiment of the present invention is illustrated. The first step is to obtain the culturing brush (Step 1). Next, unhook a catheter from an intravenous supply so that the culturing brush can be inserted within said indwelling line with the brush tip inserted first (Step 2). It may be helpful, but is not required, that the line be held in a straight angle in order to lessen the resistance of said culturing brush. The third step is to swab the flexible hub of the catheter with alcohol in order to sterilize the catheter before inserting the brush (Step 3). Thereafter, follow Steps 2-5 as shown in FIG. 3, but before culturing the brush tip, reconnect the catheter to the intravenous supply and restart the intravenous fluids (Steps 4-8).

Figure 7:
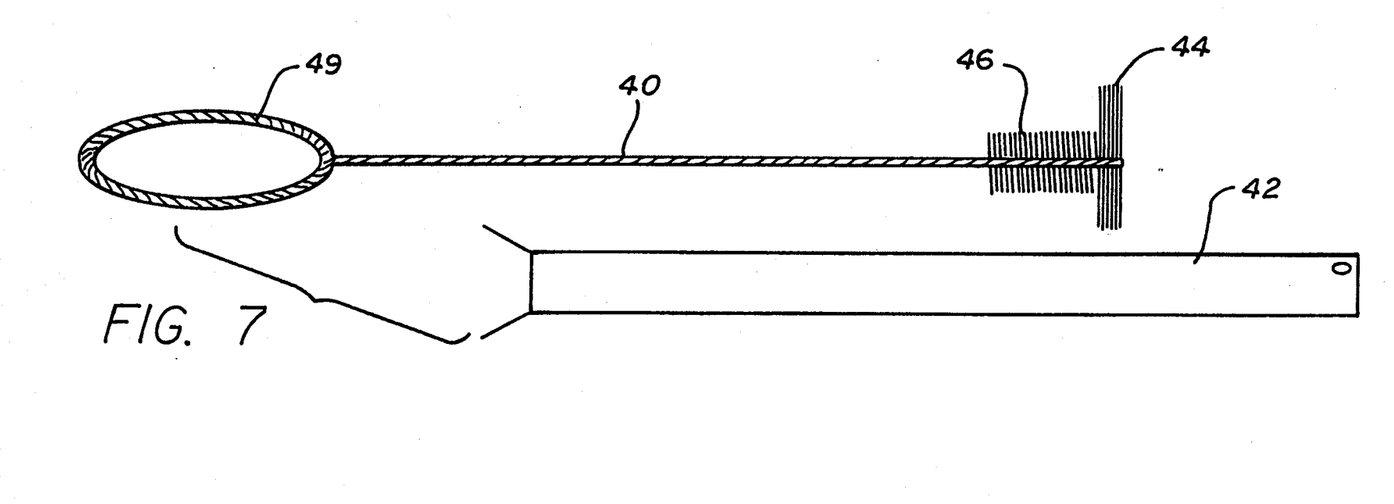
FIG. 7 is a side view of the embodiment of FIG. 5 and a schematic view of a catheter.
Figure 8:
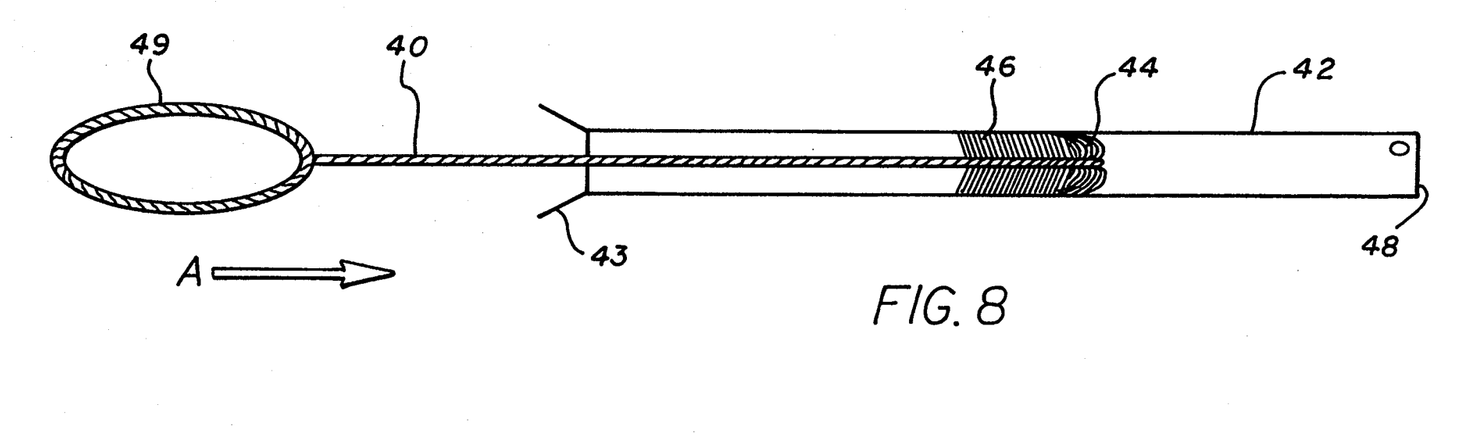
FIG. 8 is a side schematic view of the catheter and brush of FIG. 7, with the brush being inserted into the catheter.
Figure 9:
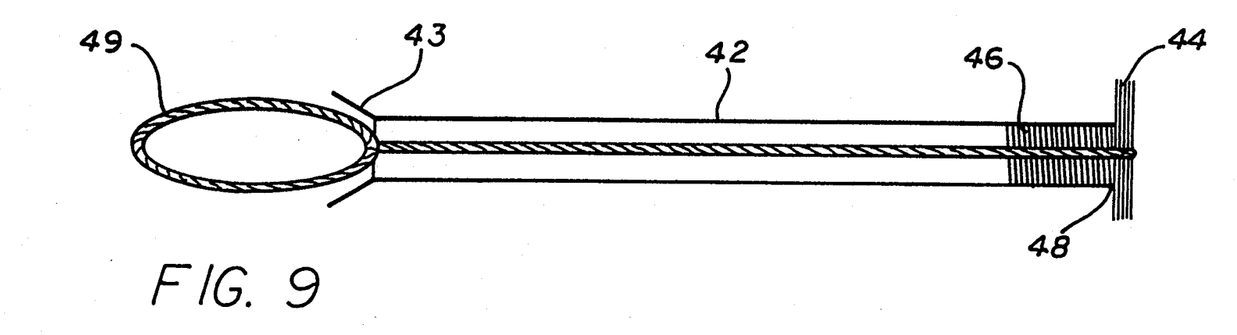
FIG. 9 is a side schematic view of the catheter and brush of FIG. 7, where the brush is fully inserted into the catheter.
Figures 9A, 10:
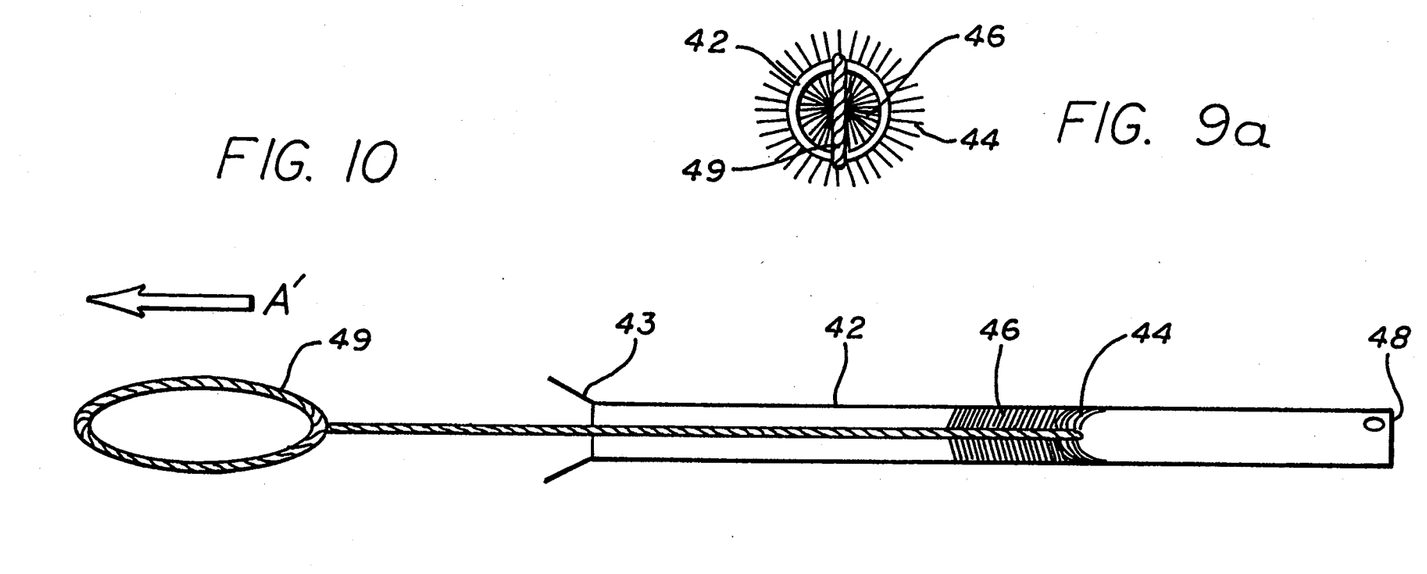
FIG. 9a is a left end view of the brush and catheter of FIG. 9.
FIG. 10 is a side schematic view of the catheter and brush of FIG. 7, where the brush is being removed from the catheter.

The method is also demonstrated in FIGS. 7-10. FIG. 7 shows a brush 40 and catheter 42 in generally schematic form. FIG. 8 shows the brush 40 being inserted into the catheter 42 in the direction A depicted by the arrow. It is noted that the larger bristles 44 are folded and the smaller bristles 46 are sized to generally touch the inside surfaces of the catheter. As shown in FIG. 9, the larger bristles 44 are outside the end 48 of the catheter 42, and the handle 49 of the brush 40 is abutting the other end 43 of the catheter, preventing the brush from being pushed further through the catheter. In this position, the larger bristles 44 can sample the outer portion of the end 48 of the catheter 42. As shown in FIG. 10, the brush 40 is then removed from the catheter in direction A′, taking with it a sample of fibrin from the outer surface of the end catheter as well as from the inner surface of the catheter. FIG. 9a shows an end view of the catheter and brush of FIG. 9, and particularly, the handle 49, the catheter 42, the larger bristles 44 outside the catheter, and the smaller bristles 46 inside the catheter.

If it is determined that infectious microbes are present in the culture, the catheter can then be removed and replaced, and the microbes can be identified, and the patients treated with the requisite antibiotics or the like. If it is determined that there is no infection, there is no need to remove the catheter, and other sources of the infection can be explored.

Figures 11, 12, 13:
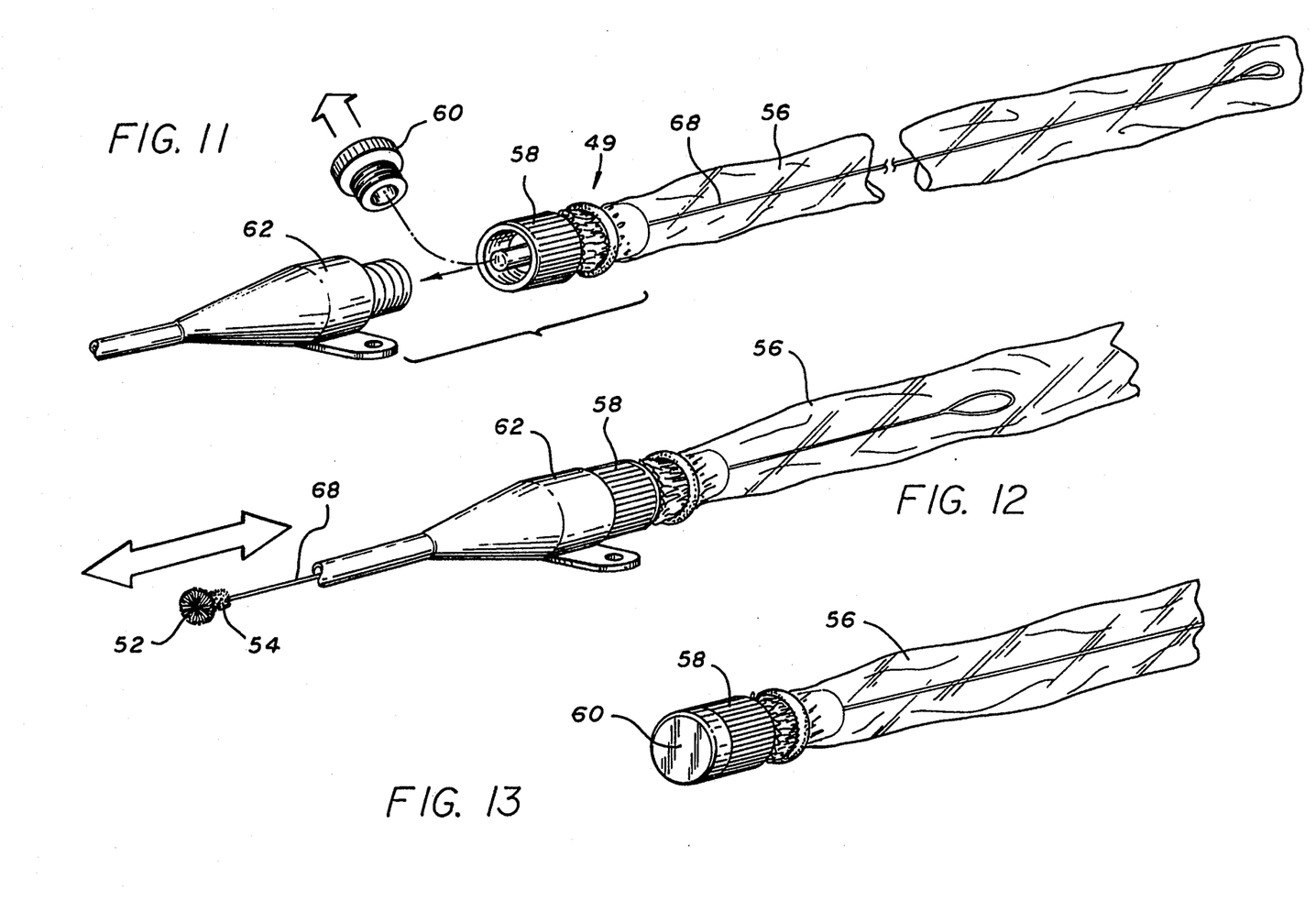
FIG. 11 is a side perspective view of an alternative embodiment of the present invention showing the cap removed, and how the present invention is attached to a catheter.
FIG. 12 is another side perspective view of the alternative embodiment of the present invention shown in FIG. 11, showing the present invention attached to the catheter, and the brush being passed through the catheter.
FIG. 13 is another side perspective view of the alternative embodiment of the present invention shown in FIG. 11, showing the present invention with a cap disposed thereon.

As shown in FIGS. 11-13, an alternative embodiment of the present invention, generally referred to as element 49, is disclosed. The embodiment comprises the brush 50 of the type previously described, which brush may have a bristle arrangement as described above with the end bristles 52 being longer then the adjacent bristles 54, or the bristles may all be of the same length. This embodiment comprises a bag 56 made of a plastic material capable of being sterilized, the bag being attached to a luer-lock coupling device 58 with a hollow tube-like extension 59, or other similar attachment means, and a cap 60, preferably with a luer-lock attachment, for coupling to said luer-lock coupling device 58, for secure and sterile coupling of the cap to the remainder of the assembly. The bag 56 may be attached to the luer-lock coupling 58 by a rubber ring 61, or by any other attachment means. As shown in FIG. 11, when the cap 60 is removed, the catheter 62, which is typically fitted with a luer-lock coupling device, may be attached to the apparatus 49.

As shown in FIG. 12, after the catheter 62 and the luer-lock coupling device 58 are secured, the brush 50 is advanced through the catheter 62 to take the sample as previously described. The catheter 62 is shown in a cutaway view to illustrate the advancing brush. As previously described the brush 50 is disposed on the wire 68.

As shown in FIG. 13, after the sample is taken, the brush is withdrawn back into the bag 56 and the cap 60 is replaced.

The apparatus described herein may be manufactured by many different materials and many different sizes. For example, the device can be manufactured as a single unit or as a plurality of units coupled together. Moreover, it can be made of stainless steel, plastic or any other material which can be sterilized. While the method and apparatus have been described in terms of various embodiments, other embodiments may come to mind to those skilled in the art without departing from the spirit and scope of the present invention. The invention should, therefore, be measured in terms of the claims which follow.

What I claim is:

1. A method for detecting whether a catheter is the cause of an infection, said catheter having an inner surface and an inlet at one end of said catheter and at least one outlet at the other end of said catheter, said method comprising the steps of:
   providing a means for collecting fibrin, said collecting means comprising a brush with a microbial protective barrier means disposed around the brush and a cap means disposed on the end of said barrier means adjacent said brush;
   removing said cap means;
   coupling said barrier means to said catheter at said one end thereof;
   inserting said means for collecting fibrin through said inlet of said catheter and simultaneously removing said means for collecting fibrin from said protective barrier means;
   advancing said means for collecting fibrin toward said at least one outlet until at least a portion of said brush extends through said at least one outlet;
   removing said means for collecting fibrin from said inlet of said catheter and taking a sample of fibrin from the inner surface of said catheter and outside the outlet of said catheter; and
   culturing the sample of fibrin collected on said means for collecting fibrin to determine whether any infectious microbes were disposed in said fibrin.

2. The method according to claim 1 further comprising identifying said infectious microbes.

3. The method according to claim 1 wherein if an infection is detected, the catheter is removed.

4. The method according to claim 1 wherein said protective barrier means comprises a plastic bag with an open end disposed over said brush, said open end having a luer-lock connector thereon for coupling said barrier means to said catheter, and said cap means is removably coupled to said luer-lock connector.

5. The method according to claim 4 wherein after the sample is taken, the brush means is withdrawn into said plastic bag and the cap is replaced on the luer-lock connector and locked thereon to maintain the viability of any infectious microbes disposed with said sample of fibrin.

6. The method accord to claim 1 wherein prior to connecting said means for collecting fibrin to said catheter, said inlet of said catheter is sterilized.

7. The method according to claim 1 wherein said sample is cultured by plating said sample onto a culture medium.

8. A method for detecting whether a catheter is contaminated and thereby is the cause of an infection, said catheter having an inner surface and an inlet at one end of said catheter and at least one outlet at the other end of said catheter, said method comprising the steps of:

supplying an apparatus for collecting fibrin, said apparatus comprising a flexible, sterile wire having a brush means on an end thereof, and a protective bag means disposed over said wire and brush means, said protective bag means having a luer-lock connector disposed at the end adjacent the brush means;

disconnecting said one end of said catheter from an intravenous supply;

connecting said luer-lock connector of said bag means to said catheter at said one end thereof;

inserting said brush means through said inlet of said catheter;

moving said brush means from said inlet toward said at least one outlet until at least a portion of said brush means extends through said at least one outlet;

removing said brush means from said catheter and simultaneously reinserting said brush means in said protective bag, taking with said brush means a sample of fibrin disposed on the inside of said catheter and outside the outlet of the catheter;

reconnecting said one end of said catheter to said intravenous supply;

restarting said intravenous supply; and culturing said sample of fibrin to detect and identify any microorganisms therein.

9. An apparatus for detecting whether a catheter is the cause of an infection, said catheter having an inner surface and an outer surface with an inlet at one end and an outlet at an other end, and said catheter having a fibrin deposit on said inner surface, said apparatus comprising:

an extended handle of a predetermined and sufficient length to extend entirely through said catheter, said handle having a first end and a second end;

brush means for collecting a sample from said fibrin deposit on said inner surface of said catheter which brush means is disposed on said first end of said handle, said brush means having a first portion adjacent said first end of said handle and a second portion; and protective bag means comprising a sterilizable microbially impervious material disposed over said handle and brush means, a luer-lock coupling means disposed at one end adjacent said brush means and a removable cap means attachable to said luer-lock coupling means.

10. The apparatus according to claim 9 wherein said brush means comprises longer bristles on the first portion thereof and shorter bristles adjacent thereto on said second portion thereof.

* * * * *